(12) United States Patent
Boss, Jr.

(10) Patent No.: US 8,974,442 B1
(45) Date of Patent: Mar. 10, 2015

(54) FACIAL AREA REJUVENATION

(76) Inventor: William K. Boss, Jr., Hackensack, NJ (US)

( * ) Notice: Subject to any disclaimer, the term of this patent is extended or adjusted under 35 U.S.C. 154(b) by 1234 days.

(21) Appl. No.: 12/408,452

(22) Filed: Mar. 20, 2009

Related U.S. Application Data (63) Continuation of application No. 12/335,132, filed on Dec. 15, 2008, now abandoned.

(60) Provisional application No. 61/013,837, filed on Dec. 14, 2007.

(51) Int. Cl.
*A61N 5/06* (2006.01)

(52) U.S. Cl.
USPC ............. 606/2; 607/88; 607/89; 128/898

(58) Field of Classification Search
USPC .................. 128/898; 606/1; 607/88, 89
See application file for complete search history.

(56) References Cited

U.S. PATENT DOCUMENTS

| | | | | |
|---|---|---|---|---|
| 5,931,855 | A * | 8/1999 | Buncke | 606/228 |
| 6,176,854 | B1 * | 1/2001 | Cone | 606/15 |
| 2004/0049251 | A1 * | 3/2004 | Knowlton | 607/101 |

OTHER PUBLICATIONS

Dedo, D.D. (Mar. 1986). "Liposuction and the Platysma Muscle," *Arch Otolaryngol Head Neck Surg.* 112: 306-308.
Robbins, L.B. and Shaw, K.E. (Jan. 1989). "En Bloc Cervical Lipectomy for Treatment of the Problem Neck in Facial Rejuvenation Surgery," *Plastic and Reconstructive Surgery* 83(1): 53-60.
Asken, S. (Jul. 1990). "Perils and Pearls of Liposuction," *Dermatologic Clinics* 8(3): 415-419.
Goddio, A.S. (Jan. 1991). "Skin Retraction Following Suction Lipectomy by Treatment Site: A Study of 500 Procedures in 458 Selected Subjects," *Plastic and Reconstructive Surgery* 87(1): 66-75.
Dillerud, E. (Aug. 1991). "Suction Lipoplasty: A Report on Complications, Undesired Results, and Patient Satisfaction Based on 3511 Procedures," *Plastic and Reconstructive Surgery* 88(2):239-249. [and invited comment from (May 1992) *Plastic and Reconstructive Surgery* 89(5):996-998.]
Kamer, F.M. (Feb. 1993). "Postoperative Platysmal Band Deformity," *Arch Otolaryngol Head Neck Surg.* 119: 193-196.
Perkins, S.W. (Feb. 1993). "Use of Submentoplasty to Enhance Cervical Recontouring in Face Lift Surgery," *Arch Otolaryngol Head Neck Surg.* 119:179-183.
Hamilton, J.M. (Sep. 1993). "Submental Lipectomy with Skin Excision," *Plastic and Reconstructive Surgery* 92(3): 443-447.

(Continued)

*Primary Examiner* — Aaron Roane
(74) *Attorney, Agent, or Firm* — Morrison & Foerster LLP (57) ABSTRACT

Rejuvenation of the facial area, e.g., face, neck, jowls, and the like, that combines a plurality of different modalities is disclosed. A rejuvenation method can combine such modalities as skin tightening, in which electromagnetic energy, such as radio-frequency energy, visible light, and the like, or ultrasonic energy can be applied to the skin to tighten it; tissue tightening, in which sutures can be put in repositioned, tightened tissue underlying the skin to hold the tissue in place; tissue reinforcement, in which other sutures can be put around the tissue tightening sutures to reinforce their hold on the underlying tissue; and skin resection, in which excess skin can be excised and the remaining skin anchored over the tightened underlying tissue to produce a rejuvenating effect.

2 Claims, 5 Drawing Sheets (56) References Cited

OTHER PUBLICATIONS

Giampapa, V.C. and Di Bernardo, B.E. (1995). "Neck Recontouring with Suture Suspension and Liposuction: An Alternative for the Early Rhytidectomy Candidate," *Aesthetic Plastic Surgery* 19:217-223.
Goodstein, W.A. (Nov. 1996). "Superficial Liposculpture of the Face and Neck," *Plastic and Reconstructive Surgery* 98(6): 988-996.
Rees, T.D. (Jan./Feb. 1997). "In Search of the Perfect Face Lift: A Personal Odyssey," *Aesthetic Surgery Journal* 17(1): 29-36.
Vogt, P.A. (Jan./Feb. 1997). "Superficial Liposuction Has a Steep Learning Curve and May Cause Uncorrectable Irregularities," *Aesthetic Surgery Journal* 17(1): 65-68.
Cook, W.R. (1997). "Laser Neck and Jowl Liposculpture Including Platysma Laser Resurfacing, Dermal Laser Resurfacing, and Vaporization of Subcutaneous Fat," *Dermatologic Surgery* 23:1143-1148.
Becker, D.G. et al. (Jul.-Sep. 1999). "A 3-Year Mulit-institutional Experience With the Liposhaver," *Arch Facial Plastic Surgery* 1:171, 173, 175.
Sullivan, C.A. et al. (Feb. 1999). "Complications of Rhytidectomy in an Otolaryngology Training Program," *Triological Society Papers* 109(2, Part 1): 198-203.
Cook, W.R. (Oct. 1999). "Cook Weekend Alternative to the Facelift: Liposculpture of the Face, Neck, and Jowls with Laser Dermal Resurfacing and Platysmal Plication," *Dermatologic Clinics* 17(4): 773-782.
Owsley, J.Q. (Jan. 2000). "Face Lifting: Problems, Solutions, and an Outcome Study," *Plastic and Reconstructive Surgery* 105(1): 302-313.
Jacob, C.I. et al. (Jul. 2000). "Liposuction and Surgical Recontouring of the Neck: A Retrospective Analysis," *Dermatologic Surgery* 26(7): 625-632.
Grotting, J.C. and Beckenstein, M.S. (Mar. 2001). "Cervicofacial Rejuvenation Using Ultrasound-Assisted Lipectomy," *Plastic and Reconstructive Surgery* 107(3):847-855.
Morrison, W. and Mladick, R. (2001). "The Minimal Facelift: Liposuction of the Neck and Jowls," *Aesthetic Plastic Surgery* 25:94-99.
Noodleman, F.R. and Harris, D.R. (Jun. 2002). "The Laser-Assisted Neck Lift: Modifications in the Technique and Postoperative Care to Improve Results," *Dermatologic Surgery* 28(6):453-458.
Bernard, R.W. (Nov./Dec. 2003). "The Anterior Vertical SMAS Lift," *Aesthetic Surgery Journal* 23(6): 486-494.
Wu, W.T.L. (Nov./Dec. 2004). "Barbed Sutures in Facial Rejuvenation," *Aesthetic Surgery Journal* 24(6): 582-587.
Silva-Siwady, J.G. et al. (Mar. 2005). "A Case of Aptos Thread Migration and Partial Expulsion," *Dermatologic Surgery* 31(3): 356-358.
Zins, J.E. and Fardo, D. (May 2005). "The 'Anterior-Only' Approach to Neck Rejuvenation: An Alternative to Face Lift Surgery," *Plastic and Reconstructive Surgery* 115(6): 1761-1768.
Mladick, R.A. (May/Jun. 2005). "Neck Rejuvenation Without Face Lift," *Aesthetic Surgery Journal* 25(3):285-287.
Massiha, H. (May/Jun. 2005). "Reassessing Lower Lid Anchoring After 24 Years," *Aesthetic Surgery Journal* 25(3):288-291.
Nahai, F. (May/Jun. 2005). "Transconjunctival Upper Lid Blepharoplasty," *Aesthetic Surgery Journal* 25(3):292-300.
Brandy, D.A. (2005). "The QuickLift: Featuring an Encircling Double Purse-String Plication Technique With Blunt Neck/Jowl Undermining and Small Submental Tuck for Tightening the Sagging Superficial Musculoaponeurotic System, Platysma, and Skin," *The American Journal of Cosmetic Surgery* 22(4): 223-232.
Cuzalina, L.A. and Koehler, J. (2005). "Submentoplasty and Facial Liposuction," *Oral Maxillofacial Surgery Clinics of North America* 17(1): 85-98.
Haiavy, J. and Leventhal, M.S. (2005). "Facial Rejuvenation With Barbed Sutures: A Retrospective Analysis of Technique and Results," *The American Journal of Cosmetic Surgery* 22(4): 239-247.

Ichikawa, K. et al. (2005). "Histologic Evaluation of the Pulsed Nd:YAG Laser for Laser Lipolysis," *Lasers in Surgery and Medicine* 36: 43-46.
Noone, R.B. (Mar. 2006). "Suture Suspension Malarplasty with SMAS Plication and Modified SMASectomy: A Simplified Approach to Midface Lifting," *Plastic and Reconstructive Surgery* 117(3): 792-803.
DeLorenzi, C.L. (Mar./Apr. 2006). "Barbed Sutures: Rationale and Technique," *Aesthetic Surgery Journal* 26(2): 223-229.
Prado, A. et al. (Apr. 2006). "A Clinical Retrospective Study Comparing Two Short-Scar Face Lifts: Minimal Access Cranial Suspension versus Lateral SMASectomy," *Plastic and Reconstructive Surgery* 117(5): 1413-1425.
Stuzin, J. (Apr. 2006). "A Clinical Retrospective Study Comparing Two Short-Scar Face Lifts: Minimal Access Cranial Suspension versus Lateral SMASectomy," *Plastic and Reconstructive Surgery* 117(5): 1426-1427.
Paul, M.D. (May 2006). "The Evolution of the Midface Lift in Aesthetic Plastic Surgery," *Plastic and Reconstructive Surgery* 117(6): 1809-1827.
Prado, A. et al. (Sep. 2006). "A Prospective, Randomized, Double-Blind, Controlled Clinical Trial Comparing Laser-Assisted Lipoplasty with Suction-Assisted Lipoplasty," *Plastic and Reconstructive Surgery* 118(4): 1032-1045.
Rohrich, R.J. et al. (Oct. 2006). "Neck Rejuvenation Revisited," *Plastic and Reconstructive Surgery* 118(5): 1251-1263.
Goldman, A. (2006). "Submental Nd:YAG Laser-Assisted Liposuction," *Lasers in Surgery and Medicine* 38:181-184.
Haack, J. and Friedman, O. (2006). "Facial Liposculpture," *Facial Plastics Surgery* 22(2):147-153.
Lee, C.J. et al. (Feb. 2007). "Dyesthesia and Fasciculation: Unusual Complications Following Face-Lift with Cog Threads," *Dermatologic Surgery* 33(2): 253-255.
Waterhouse, N. et al. (Mar. 2007). "Modified Lateral SMASectomy," *Plastic and Reconstructive Surgery* 119(3): 1021-1026.
Baker, D.C. (Mar. 2007). "Modified Lateral SMASectomy," *Plastic and Reconstructive Surgery* 119(3): 1027-1028.
Höfling, C.C. et al. (Apr. 2007). "Infection of Polypropylene Threads for Face-Lifting with *Mycobacterium fortuitum*," *Dermatologic Surgery* 33(4):492-495.
Serra-Renom, J.M. et al. (Jan. 2008). "Inferiorly Pedicled Tongue-Shaped SMAS Flap Transposed to the Mastoid to Improve the Nasolabial Fold and Jowls and Enhance Neck Contouring during Face-Lift Surgery," *Plastic and Reconstructive Surgery* 121(1): 298-304.
Mordon, S.R. et al. "Mathematical Modeling of Laser Lipolysis," located at http://biomedical-engineering-online.com/content/7/1/10 published on Feb. 29, 2008. (13 pages).
Tanna, N. and Lindsey, W.H. (Feb. 2008). "Review of 1,000 Consecutive Short-Scar Rhytidectomies," *Dermatologic Surgery* 34(2): 196-203.
Villa, M.T. et al. (Mar. 2008). "Barbed Sutures: A Review of the Literature," *Plastic and Reconstructive Surgery* 121(3): 102e-108e.
Guerrerosantos, J. (Mar./Apr. 2008). "Managing Platysma Bands in the Aging Neck," *Aesthetic Surgery Journal* 28(2): 211-216.
Marchac, D. (Mar./Apr. 2008). "Against the 'Visible' Short Scar Face Lift," *Aesthetic Surgery Journal* 28(2): 200-210.
Brandy, J. (2008). "Reality is . . . Cosmetic Business is BOOMING," QuickLiftMD.com. (2 pages).
Kaminer, M.S. et al. (2008). "Long-Term Efficacy of Anchored Barbed Sutures in the Face and Neck," *Dermatologic Surgery* 34:1-7.
Loftus, J.M. (2008). *The Smart Woman's Guide to Plastic Surgery*. McGraw Hill: New York, NY.
Gentile, R. "SmartLifting: A Technological Innovation for Facial Rejuvenation," Youngstown, OH.

\* cited by examiner

FACIAL AREA REJUVENATION

FIELD OF THE INVENTION

This relates to facial area cosmetic procedures and, more particularly, to facial area rejuvenation methods comprising a plurality of different modalities.

BACKGROUND OF THE INVENTION

Several procedures have been developed for facelifts. The most common procedure, known as a standard facelift procedure, can involve making an incision along the hairline beginning at the temple, down and around the ear, and along the hairline ending at the back of the neck; elevating (or separating) the skin from the underlying tissue; tightening the underlying tissue with sutures; optionally, removing excess tissue and/or fat; redraping the skin over the tightened underlying tissue; and resecting (or excising) any excess redraped skin. Concerns with the standard procedure have been that it elevates a great deal of skin, which can potentially lead to nerve damage, skin loss or death, hematoma, infection, or nerve paralysis, that it takes about 4 to 6 weeks for swelling to go down, which can limit the activities of the patient, and that it takes up to 4 hours to complete as a full surgical procedure under general aesthesia.

Another procedure known as a short scar facelift procedure was developed to reduce the size of the incision and hence the potential scarring from the standard procedure. The short scar facelift procedure and like variations thereof are sometimes referred to as a minimal incision lift, an S-lift, a Macs-lift, an O-lift, a quick lift, and a lifestyle lift. The short scar facelift procedure can involve making an incision along the hairline beginning at the temple and down the front of the ear ending either mid-ear or at the earlobe; elevating the skin from the underlying tissue at the incision to the zygomatic arch; tightening the underlying tissue with sutures; redraping the elevated skin over the tightened underlying tissue; and optionally, resecting the skin, all done under local aesthesia. This procedure is more limited in the facial areas for which it works compared to the standard procedure. Neither does it generally remove excess tissue and/or fat.

Another procedure known as a thread facelift procedure was developed to produce almost no scarring compared to the standard procedure. The thread facelift procedure can involve making a very small incision, e.g., about 2 cm, at the ear; elevating the skin from the underlying tissue only enough to access the underlying tissue; passing barbed threads, e.g., contour, feather lift, silhouette, and the like, into the underlying tissue; tightening the threads to provide an upward pull on the underlying tissue; and redraping the elevated skin over the tightened underlying tissue, all under local aesthesia. This procedure can provide minimal incisions, bruising, and swelling and faster recovery. However, it generally does not provide a long-term fix, offers only modest improvements, and does not remove excess tissue or skin.

Another procedure known as the nonsurgical facelift procedure was developed as an alternative to invasive surgery. The nonsurgical facelift procedure can involve externally applying electromagnetic energy, such as radio-frequency energy, or ultrasonic energy to the skin, thereby stimulating the skin to tighten on its own. This procedure can reduce wrinkles and allows the patient to recover in merely a day. However, it generally only works for a patient with modest skin laxity or wrinkles and can take as long as 6 months for the skin to tighten enough to see noticeable improvement.

Another procedure known as an open neck lift procedure was developed to target the neck area, either alone or in combination with the face. The open neck lift procedure can involve making a large incision under the chin and a smaller incision behind the ear; elevating the skin from the underlying tissue; tightening the underlying tissue in the neck with sutures; removing excess tissue and/or fat in the neck; inserting interlocking sutures in the neck midline area and behind the ear to pull up and further tighten the neck muscles; redraping the skin over the tightened underlying tissue; and resecting any excess redraped skin. However, the open neck lift procedure has similar concerns as the standard facelift procedure.

Accordingly, there is a need for a procedure that overcomes the shortcomings of existing procedures and provides an improved and longer lasting rejuvenating effect.

SUMMARY OF THE INVENTION

This relates to rejuvenation of the facial area, e.g., face, neck, jowls, and the like, using a method that combines a plurality of different modalities. In some embodiments, a skin tightening modality can be applied to the facial area, in which electromagnetic energy, such as radio-frequency energy, visible light, and the like, or ultrasonic energy can be applied internally to the skin to tighten it. In some embodiments, a tissue tightening modality can be applied to the facial area, in which barbed sutures or the like can be put in repositioned, tightened tissue underlying the skin to hold the tissue in place. In some embodiments, a tissue reinforcement modality can be applied to the facial area, in which other sutures can be put around the tissue tightening sutures to reinforce their hold on the underlying tissue. In some embodiments, a skin resection modality can be applied to the facial area, in which excess skin can be excised and the remaining skin anchored over the tightened underlying tissue to produce a rejuvenating effect.

This further relates to a system for rejuvenation of the facial area. In some embodiments, the system can include a skin tightening device, such as a laser or the like, that can administer energy internally to the skin in the facial area to tighten the skin. In some embodiments, the system can include a tissue tightening device, such as a barbed suturing needle or the like, that can place barbed sutures or the like into repositioned, tightened tissue underlying the skin to hold the tissue in place in the facial area. In some embodiments, the system can include a tissue reinforcement device, such as a suturing needle or the like, that can place reinforcement sutures around tissue tightening sutures to reinforce the tightening sutures' hold on the underlying tissue in the facial area. In some embodiments, the system can include a skin resection device, e.g., a scalpel or the like, that can excise excess skin from the facial area so that the remaining skin can be anchored over the tightened underlying tissue to produce a rejuvenating effect.

DETAILED DESCRIPTION OF THE PREFERRED EMBODIMENTS

In the following description of preferred embodiments, reference is made to the accompanying drawings in which it is shown by way of illustration specific embodiments in which the invention can be practiced. It is to be understood that other embodiments can be used and structural changes can be made without departing from the scope of the embodiments of this invention.

This relates to rejuvenation of the facial area, e.g., face, neck, jowls, and the like, using a method that combines a plurality of different modalities. The method can combine such modalities as skin tightening, in which electromagnetic energy, such as radio-frequency energy, visible light, and the like, or ultrasonic energy can be applied to the skin to tighten it; tissue tightening, in which sutures can be put in repositioned, tightened tissue underlying the skin to hold the tissue in place; tissue reinforcement, in which other sutures can be put around the tissue tightening sutures to reinforce their hold on the underlying tissue; and skin resection, in which excess skin can be excised and the remaining skin anchored over the tightened underlying tissue to produce a rejuvenating effect. The method can be performed under local anesthesia and in approximately half the time as standard facelift methods. Moreover, the method can minimize the extent of facial skin elevation compared to standard methods. Furthermore, the method can provide an improved look and longer lasting effect over standard methods.

Although some embodiments of this invention may be described herein in terms of rejuvenation of the facial area, it should be understood that embodiments of this invention are not so limited, but are generally applicable to any body area that can benefit from cosmetic procedures.

Figure 1:
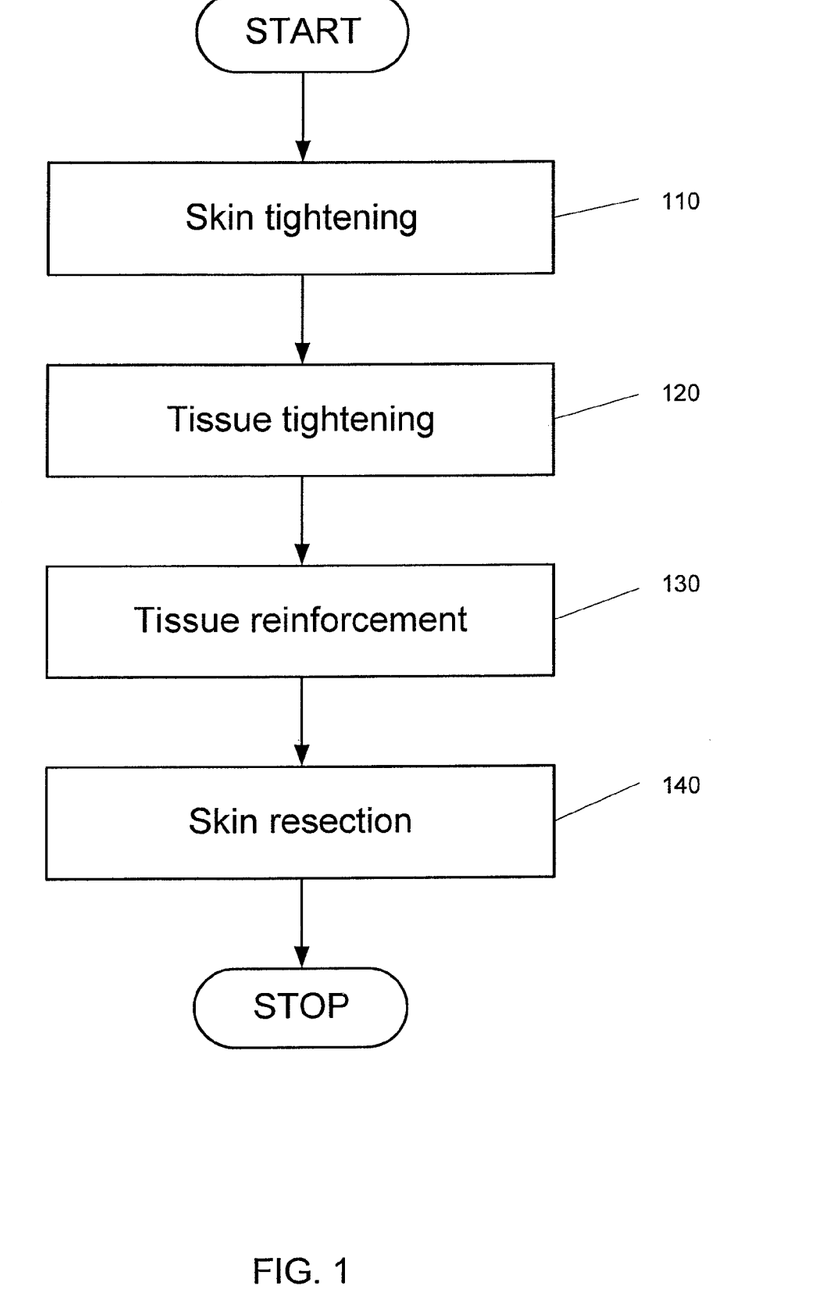
FIG. 1 illustrates an exemplary method for facial area rejuvenation according to embodiments of the invention.
Figure 2:
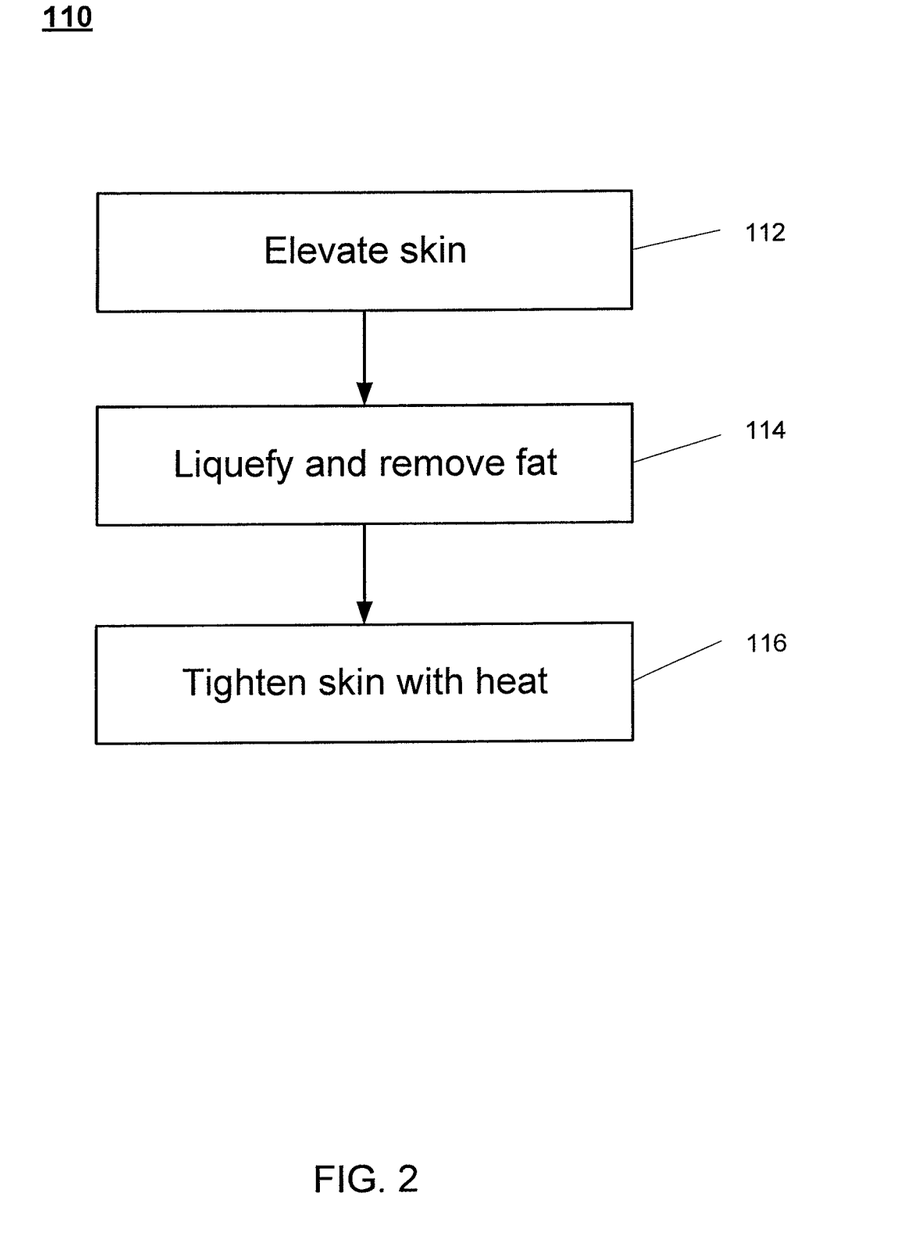
FIG. 2 illustrates an exemplary skin tightening modality of the method of FIG. 1 according to embodiments of the invention.

FIG. 1 illustrates an exemplary method for facial area rejuvenation according to embodiments of the invention. In the example of FIG. 1, the skin can be tightened using an energy source, such as an electromagnetic energy source, e.g., radio-frequency energy, visible light, and the like, or an ultrasonic energy source (110). FIG. 2 illustrates an exemplary skin tightening modality of the method of FIG. 1 according to embodiments of the invention. In the example of FIG. 2, the skin in the facial area can be elevated or lifted away from the underlying tissue (112). This can be done by making an incision into the skin and separating the skin, beginning at the incision, from the underlying tissue. In some embodiments, for the face and jowls, an incision can be made along the hairline down to the middle portion of the ear or to the earlobe. The skin can be elevated from the incision area to the lateral corner of the eye in a perpendicular drop from the forehead past the lateral eye down to the jaw line, thereby separating from the underlying superficial muscular aponeurotic system (SMAS). In some embodiments, for the neck, an incision can be made along the hairline in the neck area behind the ear above the sternocleidomastoid muscle. The skin can be elevated from the incision area along the sternocleidomastoid muscle, thereby separating from the underlying platysma tissue. In some embodiments, for the face, jowls, and/or neck, an incision can be made under the chin. The skin can be elevated from the incision area back toward the neck, thereby separating from the underlying tissue. In general, an objective can be to elevate only as much skin as is necessary to achieve facial rejuvenation and avoid significant swelling.

In some embodiments, a laser can be used to elevate the skin. The laser can make an incision into the skin and then move into the incision under the skin to separate the skin from the underlying tissue. The laser can administer energy internally to the affected area, e.g., under the skin, to perform the separation. For example, a Cool Touch® laser or a Cool Lipo® laser can emit a continuous or pulsed high power beam at a 1320 nm wavelength to make the incision and short, high power pulses at either the same or a different wavelength to elevate the skin. Alternatively, a SmartLipo® laser can emit a continuous or pulsed high power beam at a 1064 nm wavelength to make the incision and short, high power pulses at either the same or a different wavelength to elevate the skin. Other emission wavelengths can also be utilized. Other energy devices can also be utilized, such as diodes. Other energy sources can also be used, such as radio-frequency energy, ultrasonic energy, and the like.

The facial area can be subjected to lipolysis to liquefy and remove excess fat from the subcutaneous fat layer under the skin (114). This can be done by inserting a lipolysis device through the incision and under the skin to target subcutaneous fat, delivering enough heat to the fat to liquefy it, and suctioning out the liquefied fat. The lipolysis device can administer heat internally to the affected area, e.g., under the skin, to liquefy the subcutaneous fat. In some embodiments, for the face and jowls, a lipolysis device can be inserted into the cheek and jowl area to remove excess fat. In some embodiments, for the neck, a lipolysis device can be inserted into the submental area and in the sternocleidomastoid muscle area to remove excess fat. In some embodiments, for the face, jowls, and/or neck, a lipolysis device can be inserted underneath the chin area to remove excess fat. Where fat should be targeted can be determined by observation or by feel.

In some embodiments, the laser used to elevate the skin can be used to liquefy and remove excess fat. For example, as the laser moves under the skin and emits short, high power pulses internally into the affected area to separate the skin from the underlying tissue, surrounding subcutaneous fat can absorb some of the laser's energy and convert the energy to heat, thereby catabolyzing, softening, and liquefying the fat. Alternatively, for example, the laser can complete a first pass to elevate the skin and a second pass to liquefy the fat. The laser can have a small liposuction cannula, e.g., 2-3 mm diameter, through which to suction out the liquefied fat. Alternatively, a separate liposuction cannula can be inserted into the incision to suction out the liquefied fat after the laser completes the liquefaction.

The skin in the facial area can be tightened (116). This can be done by inserting a heating device through the incision and under the skin to target the elevated skin's undersurface and delivering enough heat to stimulate collagen formation that tightens the skin. The heating device can administer heat internally to the affected area, e.g., under the skin, to tighten the skin.

In some embodiments, the laser used to elevate the skin and liquefy excess fat can be used to tighten the skin. For example, as the laser moves under the skin to separate the skin from the underlying tissue, the skin can absorb some of the laser's energy and tighten. Laser energy at a 1320 nm wavelength can be more readily absorbed by water in the skin; whereas, laser energy at a 1064 nm wavelength can be more readily absorbed by blood in blood vessels in the skin. Alternatively, for example, the laser can complete first pass(es) to elevate the skin and liquefy excess fat and a subsequent pass to tighten the skin. In some embodiments, rather than applying the laser internally to the skin's undersurface, the laser can be applied externally to the surface of the skin to tighten the skin. In which case, a cooling device may be used concurrently with the laser to cool the skin surface. Examples of cooling devices can include a water sprayer to mist water over the skin surface and a cool air fan to blow air over the skin surface.

The duration and frequency of the laser pulses and the duration and vacuum pressure of the cannula can vary depending on a variety of factors, such as the patient, the amount of fat, the facial area, and so on.

Although some embodiments describe utilizing a laser for the energy skin tightening modality, embodiments of the invention are not so limited. Rather, any electromagnetic device, e.g., a diode, capable of providing sufficient energy to do the skin tightening can be utilized according to embodiments of the invention. Similarly, any other energy source, e.g., an ultrasonic device, capable of providing sufficient energy to do the skin tightening can be utilized according to embodiments of the invention.

Figure 3:
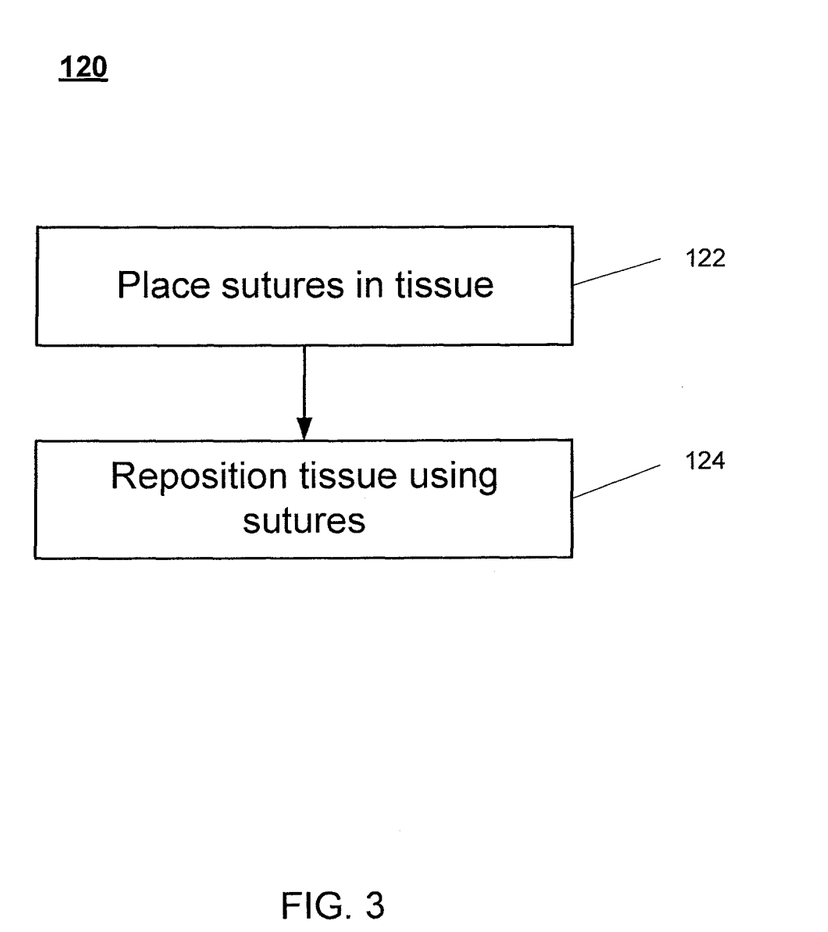
FIG. 3 illustrates an exemplary tissue tightening modality of the method of FIG. 1 according to embodiments of the invention.

Referring back to FIG. 1, after the skin is tightened using a laser or another suitable electromagnetic or other energy device, the underlying tissue can be tightened using sutures (120). FIG. 3 illustrates an exemplary tissue tightening modality of the method of FIG. 1 according to embodiments of the invention. In the example of FIG. 3, the elevated skin can be retracted or pulled back to expose the underlying tissue. Barbed sutures can be placed in the underlying tissue (122). The underlying tissue can be pulled by the holding devices on the sutures, such as barbs or the like, into a tightened reposition and held there (124). This can be done by threading barbed sutures through the underlying tissue using standard suturing tools and techniques and pulling the sutures and the underlying tissue back to tighten. In some embodiments, for the face and jowls, sutures can be placed in and/or below the SMAS to hold the SMAS in a tightened reposition. Alternatively, sutures can be placed in and/or below the SMAS and the malar fat pad to hold them in a tightened reposition. In some embodiments, for the neck, sutures can be placed in the platysma tissue to hold it into a tightened reposition.

In some embodiments, non-absorbable threading sutures such as contour barbed sutures, silhouette-type sutures, notched-type sutures, or feather lift-type sutures can be utilized. The spacing and number of sutures can vary depending on a variety of factors, such as the patient, the facial area, and the amount of repositioning. Barbed and other types of sutures capable of performing according to embodiments of the invention can be utilized.

Figure 4:
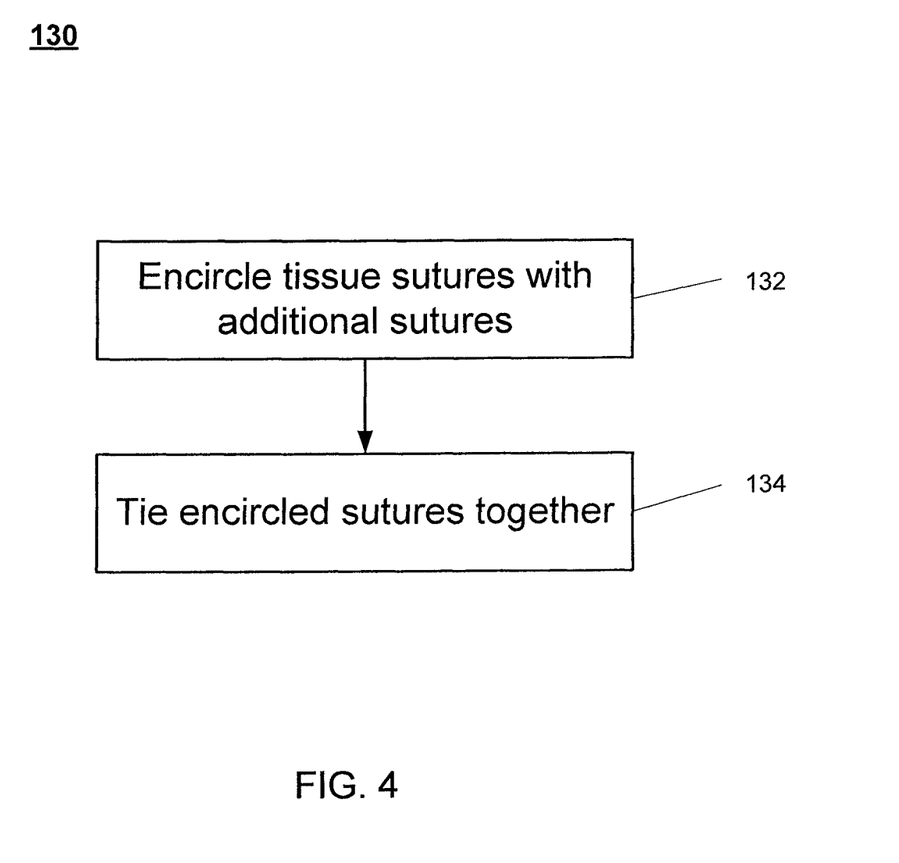
FIG. 4 illustrates an exemplary tissue reinforcement modality of the method of FIG. 1 according to embodiments of the invention.

Referring again to FIG. 1, after the underlying tissue is tightened using barbed sutures, the sutures can be reinforced with additional sutures to further tighten the tissue and attenuate the tension on the barbed sutures due to their tightening function (130). FIG. 4 illustrates an exemplary tissue reinforcement modality of the method of FIG. 1 according to embodiments of the invention. In the example of FIG. 4, the barbed sutures in the underlying tissue can be encircled by additional sutures (132). The encircling sutures can pull back the underlying tissue sutures and tie them together, further repositioning the underlying tissue to tighten (134). This can be done by threading the additional sutures through the underlying tissue sutures in a looping or encircling manner using standard suturing tools and techniques and using the additional sutures to tie the underlying tissue sutures together, thereby pulling them back toward the hairline, the anterior ear, and/or the posterior ear to tighten the tissue. The additional sutures can create secondary reinforcement of the tissue sutures so that the tissue tightening does not rest solely on the tissue sutures. The additional sutures can also take on some of the tension created by the tissue tightening in a redistributing manner. In some embodiments, for the face and jowls, additional sutures can be placed around the SMAS sutures to further tighten the SMAS. In some embodiments, for the neck, additional sutures can be placed around the platysma sutures to further tighten the platysma tissue. The sets of sutures can be anchored to the preauricular fascia, the mastoid fascia, or the deep temporal fascia.

In some embodiments, non-absorbable smooth sutures such as nylon or prolene-type sutures can be utilized. The spacing and number of sutures can vary depending on a variety of factors, such as the patient, the facial area, and the underlying tissue sutures. Other types of encircling sutures capable of performing according to embodiments of the invention can also be utilized.

Figure 5:
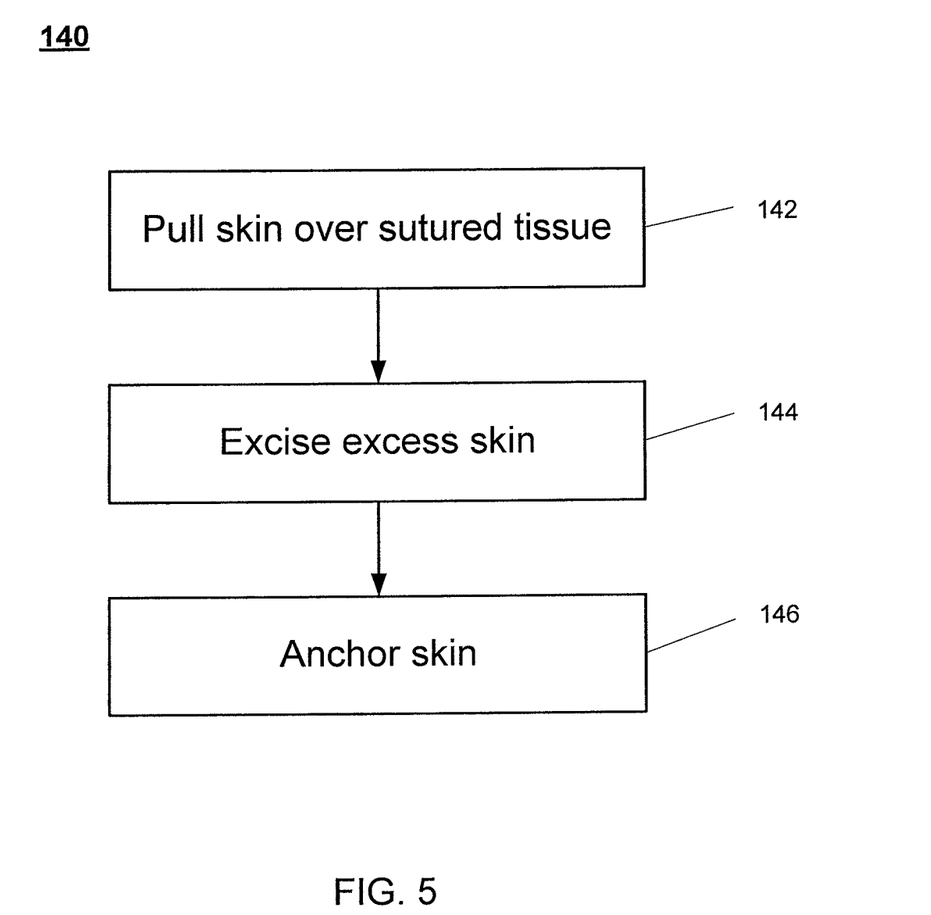
FIG. 5 illustrates an exemplary skin resection modality of the method of FIG. 1 according to embodiments of the invention.

Referring back to FIG. 1, after the underlying tissue sutures are reinforced with additional sutures, the skin can be resected to remove any excess skin and anchored in place (140). FIG. 5 illustrates an exemplary skin resection modality of the method of FIG. 1 according to embodiments of the invention. In the example of FIG. 5, the elevated and tightened skin can be redraped over the sutured underlying tissue (142). Since the above modalities will have tightened the facial area, all of the elevated skin may not be needed to cover the facial area. As such, the skin in excess of that needed to cover the facial area can be excised (144). The remaining skin can be anchored into position (146). This can be done by redraping the skin over the underlying tissue, removing the excess skin, and suturing the redraped skin in position. In some embodiments, for the face and jowls, the skin can be positioned at the supraauricular point in the scalp and anchored with sutures or staples behind the ear. In some embodiments, for the neck, the skin can be positioned near the infraauricular point in the neck and anchored with sutures or staples behind the ear.

It can be beneficial to use at least three of the modalities illustrated in FIG. 1 to advantageously provide a facial area rejuvenating effect according to embodiments of the invention. The modalities can be modified, e.g., in order of treatment, length of treatment, selection of which modalities to apply, and the like, by the doctor based on the clinical appearance of the patient.

Embodiments of the invention have several improvements over some currently utilized procedures. For example, using smaller wavelength lasers or other such devices for the energy skin tightening can avoid substantial complications that higher wavelength lasers (around 10,000 nm) currently used in some lift procedures can cause, such as skin loss, adhesions, and contractures. Using lasers or other such devices to perform internal skin tightening can help improve the rejuvenating effect. Using barbed sutures or the like to tighten underlying tissue and reinforcement sutures or the like to further do so can reduce the extent of the skin elevation in standard procedures and the recovery time. Using barbed sutures can improve the tightening of the underlying tissue compared to the short scar facelift procedure. Tightening both the SMAS, deeper tissue, and the malar fat pad with barbed sutures or the like can also improve over the short scar facelift procedure. Other advantages can be realized as well.

It is to be understood that facial area rejuvenation is not limited to the methods described here, but may include any additional or other modalities capable of providing an improved look and longer lasting rejuvenating effect according to embodiments of the invention.

EXAMPLES

These examples describe facial area rejuvenation according to embodiments of the invention that was performed during an 18-month period on 35 patients—29 women and 6 men—ranging in age from 42 to 71 years. Eleven patients underwent face rejuvenation, eight underwent neck rejuvenation, and sixteen underwent face and neck rejuvenation. Thirty-three patients were administered local aesthesia and two patients were administered intravenous sedation. The patents were tracked over an 18-month period. Results indicate that the rejuvenations held up well, that the patients were satisfied with the results, and that there were no complications or adverse effects.

Example I

Face Rejuvenation

This example describes rejuvenation of the mid-face area according to embodiments of the invention. A laser emitting a continuous or pulsed light beam at 1320 nm wavelength can be applied to a patient's face to make an incision along the patient's hairline from the temple down in front of the ear tragus to the mandible. The laser can be inserted into the incision to elevate the skin from the underlying SMAS to form a skin flap of 2 to 4 cm by administering the light beam internally, e.g., under the skin. The laser can direct, e.g., 3W, 30 to 40 Hz pulses at 30 deg C. internally to the tissue connecting the skin and SMAS to break the connections as the skin is elevated away from the SMAS. Other laser settings can also be used. This elevation can typically take 2 to 2½ minutes.

The laser can then direct, e.g., 6 to 8W, 20 to 30 Hz pulses internally to the jowls and lateral melolabial and nasolabial folds to liquefy excess subcutaneous fat in these areas for about 1½ to 3 minutes. Other laser settings can also be used. The skin temperature can be monitored with the laser temperature gauge to ensure that the temperature does not exceed 40 deg C. Optionally, the laser can be directed to the lateral cheek area to liquefy fat there. A 2 mm liposuction cannula attached to the laser can be set at a vacuum pressure of 25 mm to suction out the liquefied fat. This liquefaction and suction can typically take 2 to 4 minutes.

The laser can then direct, e.g., 8 to 12W, 30 to 40 Hz pulses internally to the undersurface of the elevated skin to tighten the skin. Other laser settings can also be used. The skin temperature can be carefully monitored to ensure that the temperature does not exceed 40 deg C. This tightening can typically take 1 to 1½ minutes.

The laser can be removed for underneath the skin and the elevated skin retracted to get to the SMAS. A set of 2 barbed non-absorbable sutures, e.g., silhouette sutures, can be placed in and/or below the SMAS in a horizontal line from the jowl area to the tragus and a second set of 2 sutures can be placed in and/or below the SMAS in a vertical line lateral to the nasolabial folds and/or into the malar fat pad. The horizontal sutures can be pulled toward the tragus and anchored at the pre-tragal fascia. The vertical sutures can be pulled toward the temple and anchored at the deep temporal fascia. This can cause the SMAS having the sutures to also be pulled and tightened. This tightening can typically take about 5 to 10 minutes.

A nylon non-absorbable suture can be looped around each of the barbed sutures for reinforcement. The nylon sutures can be pulled together to be tighter and to reinforce the barbed sutures. This can cause the SMAS having the nylon and barbed sutures to tighten even more. The nylon and barbed sutures can be anchored to the pre-tragal fascia and to the deep temporal fascia. This reinforcement can typically take about 5 to 10 minutes.

The elevated 2 to 4 cm skin flap can be redraped over the tightened SMAS toward the hairline near the supraauricular point in the scalp. The excess skin that extends past the incision point can be excised. The remaining skin can be anchored behind the ear. This can typically take 15 to 20 minutes.

The entire mid-face rejuvenation can typically take about one hour or less.

Example II

Neck Rejuvenation

This example describes rejuvenation in the neck area according to embodiments of the invention. Similar to the mid-face rejuvenation of Example I, a laser emitting a continuous or pulsed light beam at 1320 nm wavelength can be applied to a patient's neck to make one incision along the patient's hairline at the back of the neck behind the ear above the sternocleidomastoid muscle and another incision underneath the chin. The laser can be inserted into the incisions to elevate the skin from the underlying platysma tissue to form skin flaps of 1 to 2 cm by administering the light beam internally, e.g., under the skin. The laser can direct, e.g., 3W, 30 to 40 Hz pulses at 30 deg C. internally to the tissue connecting the skin and platysma tissue to break the connections as the skin is elevated away from the platysma tissue. Other laser settings can also be used. The skin can be elevated from the hairline to a line along the anterior border of the sternocleidomastoid muscle. The skin can also be elevated from the chin to near the midline neck area. This elevation can typically take 2 to 2½ minutes.

The laser can then direct, e.g., 6 to 8 W, 20 to 30 Hz pulses internally to the submental area and over the sternocleidomastoid muscle to liquefy excess subcutaneous fat in these areas for about 1½ to 3 minutes. Other laser settings can also be used. The skin temperature can be monitored to ensure that the temperature does not exceed 40 deg C. A 2 mm liposuction cannula attached to the laser can be set at a vacuum pressure of 25 mm to suction out the liquefied fat. This liquefaction and suction can typically take 2 to 4 minutes.

The laser can then direct, e.g., 8 to 12W, 30 to 40 Hz pulses internally to the undersurface of the elevated skin to tighten the skin. Other laser settings can also be used. The skin temperature can be carefully monitored to ensure that the temperature does not exceed 40 deg C. This tightening can typically take 1 to 1½ minutes.

The laser can be removed from underneath the skin and the elevated skin retracted to get to the platysma tissue. A set of 2 or 3 barbed non-absorbable sutures can be placed in a line parallel to the hairline in the platysma tissue near the ear. The sutures can be pulled upward toward the hairline to be tighter and anchored in the mastoid fascia. This can cause the platysma tissue having the sutures to also be pulled upward and tightened. Approximately one or two barbed non-absorbable sutures can be placed underneath the chin in the platysma. The sutures can be pulled together to tighten and anchored at the fascia. This tightening can typically take about 5 to 10 minutes.

A nylon non-absorbable suture can be looped around each of the barbed sutures for reinforcement. The nylon sutures can be pulled together to be tighter and to reinforce the barbed sutures. This can cause the platysma tissue having the nylon and barbed sutures to tighten even more. The nylon and barbed sutures can be anchored to the deep fascia. This reinforcement can typically take about 5 to 10 minutes.

The elevated 1 to 2 cm skin flaps can be redraped over the tightened platysma tissue toward the hairline behind the ear and underneath the chin. The excess skin that extends past the incision point can be excised. The remaining skin can be anchored behind the ear and underneath the chin. This can typically take 15 to 20 minutes.

The entire neck rejuvenation can typically take about one and one-half hours or less.

Example III

Face and Neck Rejuvenation

This example describes rejuvenation in the mid-face and neck areas according to embodiments of the invention. The rejuvenation can combine the procedures described above in Examples I and II. The rejuvenation can typically take about two and one-half hours or less.

It is to be understood that embodiments of the invention are not limited to the Examples describes herein, but can involve additional or other modalities and/or body areas suitable for rejuvenation.

Although embodiments of this invention have been fully described with reference to the accompanying drawings, it is to be noted that various changes and modifications will become apparent to those skilled in the art. Such changes and modifications are to be understood as being included within the scope of embodiments of this invention as defined by the appended claims.

What is claimed is:

1. A method of rejuvenating a facial area using multiple modalities in combination, comprising:
   applying a first modality, the first modality comprising making a minimal incision in the skin, separating the skin from underlying tissue, using laser energy to administer heat under the skin and tightening the skin of the facial area;
   applying a second modality to tighten fascia tissue underlying the skin of the facial area;
   applying a third modality to reinforce the tightening of the underlying tissue; and
   applying a fourth modality to resect excess skin of the facial area,
   wherein applying the first modality comprises at least one of using laser energy to administer heat under the skin to liquefy subcutaneous fat and using laser energy to administer heat under the skin to tighten at least one of the skin or the underlying tissue,
   wherein applying the second modality comprises:
   applying sutures to the underlying fascia tissue; and
   pulling the sutures together to cause the underlying fascia tissue to tighten,
   wherein applying the third modality comprises:
   applying sutures to the tightened underlying tissue; and
   pulling together the sutures applied to the tightened underlying tissue to cause the underlying tissue to further tighten,
   wherein applying the fourth modality comprises applying a cutting tool to the skin to resect skin in excess of the skin needed to cover the tightened underlying tissue, and
   wherein the facial area comprises at least one of a face, jowls, or neck.

2. A method of rejuvenating a facial area using multiple modalities in combination, comprising:
   applying electromagnetic energy to skin of the facial area to make a minimal incision in the skin;
   separating the skin from underlying tissue;
   using laser energy to administer heat under the skin;
   wherein using laser energy to administer heat under the skin comprises at least one of administering heat under the skin to liquefy subcutaneous fat and administering heat under the skin to tighten at least one of the skin or the underlying tissue,
   tightening the skin of the facial area;
   placing sutures in fascia tissue underlying the skin of the facial area;
   pulling the placed sutures together to cause the underlying tissue to reposition,
   reinforcing the sutures with additional sutures; wherein reinforcing the sutures comprises encircling the sutures with additional sutures and using the additional sutures to tie the encircled sutures together, and
   resecting an excess amount of the skin of the facial area, wherein resecting an excess amount of the skin comprises pulling the skin tight over the underlying tissue, resecting the pulled skin that exceeds that covering the underlying tissue, and anchoring the pulled skin covering the underlying tissue to the underlying tissue,
   wherein the facial area is at least one of a face, jowls, or neck.

* * * * *